United States Patent
Rosenberg et al.

(10) Patent No.: US 6,787,157 B1
(45) Date of Patent: Sep. 7, 2004

(54) MULTIPHASE ACTIVE INGREDIENT-CONTAINING FORMULATIONS

(75) Inventors: Joerg Rosenberg, Ellerstadt (DE); Jürgen Zeidler, Mutterstadt (DE); Jörg Breitenbach, Mannheim (DE); Gunther Berndl, Herxheim (DE); Andreas Kleinke, Ludwigshafen (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/037,792

(22) Filed: Mar. 10, 1998

(51) Int. Cl.⁷ .......................... A61K 9/10; A61K 47/32; A61K 47/38
(52) U.S. Cl. .................. 424/486; 424/487; 424/488
(58) Field of Search .................. 424/484, 489, 424/458, 469–70, 486–88

(56) References Cited

U.S. PATENT DOCUMENTS

| | | | |
|---|---|---|---|
| 4,093,709 A | * | 6/1978 | Choi et al. |
| 4,880,585 A | * | 11/1989 | Klimesch et al. |
| 5,603,960 A | * | 2/1997 | O'Hagan et al. |
| 5,741,521 A | * | 4/1998 | Knight et al. |
| 5,863,560 A | * | 1/1999 | Osborne |

FOREIGN PATENT DOCUMENTS

| | | |
|---|---|---|
| DE | 26 27 533 | 12/1977 |
| DE | 35 20 184 | 12/1985 |
| EP | 580560 | 1/1994 |
| EP | 596 203 | 5/1994 |
| EP | 598 606 | 5/1994 |
| WO | WO 93/20138 | 10/1993 |
| WO | WO 96/25149 | 8/1996 |
| WO | WO 96/29060 | 9/1996 |
| WO | WO 97/02017 | 1/1997 |

OTHER PUBLICATIONS

Bauer et al., *Pharm. Tech.*, 1993, pp. 300–303.
Voigt, "Lehrbuch der pharmazeutischen Technologie", 1987, p. 225.

* cited by examiner

*Primary Examiner*—Edward J. Webman
(74) *Attorney, Agent, or Firm*—Keil & Weinkauf

(57) ABSTRACT

A solid or semisolid, at least two-phase active ingredient-containing formulation in which there is multiparticulate incorporation of one of the two phases into a matrix of the other phase, and at least one of the phases contains at least one active ingredient, obtainable by introducing particles of one phase into the other phase in a plastic state, and shaping the material while still plastic.

4 Claims, No Drawings

MULTIPHASE ACTIVE INGREDIENT-CONTAINING FORMULATIONS

The present invention relates to solid, at least two-phase active ingredient-containing formulations in which there is multiparticulate incorporation of one of the two phases into a matrix of the other phase, and at least one of the phases contains at least one active ingredient, obtainable by introducing particles of one phase into the other phase in a plastic state, and shaping the material while still plastic. The invention furthermore relates to a process for producing such forms.

A problem which frequently occurs in pharmaceutical technology is to introduce mutually incompatible active ingredients into a drug form.

This is solved in the prior art by producing laminated or multilayered tablets. These tablet forms permit not only incompatible active ingredients to be separated but also the initial and maintenance doses to be separated in controlled release drug forms. These drug forms are normally obtained by conventional compressing. However, this requires specially designed tableting machines and at least two filling and compression stations (cf. "Pharmazeutische Technologie", Georg Thieme Verlag, 4th edition, 1993, pages 300 et seq.). This process is, however, elaborate and costly.

It is furthermore known to produce mixed granule tablets by compressing a mixture of differently pretreated granules. This entails, for example, processing untreated medicinal substances (initial dose) together with medicinal substances enveloped in fats or coated with lacquer (maintenance dose) (cf. R. Voigt, Lehrbuch der pharmazeutischen Technologie, 1987, page 225). This process is also relatively elaborate.

EP-A 580 860 discloses that it is possible to meter water or solvent in during the extrusion process. However, metering in of active ingredients is not described.

It is an object of the present invention to find a simple process for producing active ingredient-containing forms which permits the introduction of mutually incompatible active ingredients or active ingredients of different release into one drug form or the production of forms with multiphase release characteristics.

We have found that this object is achieved by the formulations defined at the outset.

It is preferred according to the invention to incorporate active ingredient-containing particles into a melt which may likewise contain active ingredient or else be free of active ingredient.

Possible particles according to the invention are granules, pellets or crystal particles, and crystal particles are preferably coated.

The particles can be obtained in a conventional way, for example by wet granulation of one or more active ingredients with conventional additives. If the active ingredient automatically results as granules in the preparation process, it can also be employed without further treatment with additives. Granules can also be obtained in a conventional way by melt extrusion of an active ingredient-containing polymer melt and subsequent shaping by hot or cold cut, prilling or drop-formation processes. Pellets can also be produced by conventional processes, for example by dry granulation. Coated or uncoated active ingredient crystals can also be obtained by processes known to the skilled worker. The particle size is not critical. For ease of handling of the particles it is advisable to use particles with a size of the order of from 0.01 to 3 mm, preferably 0.5 to 2 mm.

Particles for the purpose of this invention are also microtablets. Microtablets can likewise be produced in a conventional way.

As already mentioned, the particles can consist of pure active ingredient without containing other additives. If additive-containing particles are employed, the nature of the additives depends in particular on the release rate required for the particulate phase, ie. whether the particulate phase is to be rapid or slow release.

If coated active ingredient crystals are used, the coating may have purely stabilizing or else release-slowing properties. It is also possible to employ coatings which dissolve in particular pH ranges.

It is possible in this way to obtain combination drug forms in which the active ingredient(s) can be released from the particulate portions at various points in the digestive tract. Examples of possible coatings of this type are polyacrylates or methacrylic acid copolymers (Eudragit types).

The content of the aliquot added as particles can be from 0.01 to 90%, preferably 0.1 to 70%, particularly preferably 0.5 to 50%, of the total weight of the finished active ingredient-containing form.

In the formulation according to the invention there is multiparticulate incorporation of the particles in another phase. Thus the other phase forms the matrix for the particulate phase. The matrix phase may contain active ingredient or be free of active ingredient. An active ingredient-containing matrix phase is preferred.

It is possible in principle to employ all substances which can be melted or softened to constitute the matrix phase as long as they do not decompose under the processing conditions. The required thermoplasticity can also be brought out by adding suitable auxiliaries.

Examples of suitable constituents of the matrix are melt-processable polymeric binders. Suitable as such are uncrosslinked homo- or copolymers of N-vinylpyrrolidone with Fikentscher K values of from 12 to 120, preferably 20 to 100, with suitable comonomers preferably being vinyl esters such as vinyl propionate or vinyl butyrate or, in particular, vinyl acetate, or else N-vinylimidazole or N-vinylcaprolactam.

Further suitable binders are cellulose derivatives such as cellulose ethers, for example cellulose alkyl ethers such as methyl- or ethylcellulose or hydroxyalkylcelluloses such as hydroxypropylcellulose, also cellulose esters such as cellulose acetate, cellulose phthalate, cellulose acetate propionate, cellulose acetate phthalate or the like. Also suitable as binders are acrylate- or methacrylate-containing polymers, for example Eudragit types.

Also suitable according to the invention are matrix polymers which can be absorbed or degraded in the body. These include polylactic acid and copolymers thereof, poly (ortho)esters. Polyamides, polyphosphazenes or polyurethanes are also suitable.

Likewise suitable as matrix polymers are starch or dextrins.

Suitable matrixes according to the invention are also those composed of sugar alcohols such as erythritol, sorbitol, maltitol, mannitol, isomalt, mono- or disaccharides such as fructose or glucose.

Also suitable as matrix constituents are fatty acid glycerides and/or fatty acid polyethylene glycol esters. The latter can also be packed as semisolid extrudates with the incorporated particles into capsules. It is particularly advantageous that the softening point of these substances is relatively low and thus reliable metering in is ensured without the risk of melting the added particles. Such easily softening formulations are likewise suitable for producing suppositories and chewable compositions.

Suitable matrix polymers are also polyethylene glycols with molecular weights in the range from 1000 to 20,000.

It is furthermore possible to incorporate conventional physiologically tolerated ancillary substances into the matrix, for example bulking agents, lubricants, mold release agents, plasticizers, blowing agents, stabilizers, dyes, flavorings or flow regulators.

Examples of bulking agents are inorganic bulking agents such as the oxides of magnesium, aluminum, silicon, titanium etc. in a concentration of from 0.01 to 50, preferably from 0.20 to 20, % of the total weight of the drug form.

Examples of lubricants are stearates of aluminum, calcium and magnesium, and talc and silicones in a concentration of from 0.1 to 5, preferably from 0.1 to 3, % of the total weight of the form.

Examples of disintegration promoters which can be employed are sodium carboxymethyl starch and crospovidone. It is also possible to employ wetting agents such as sodium lauryl sulfate and sodium docusate. Salts such as $Na_2CO_3$ or $NaHCO_3$ can also be employed.

Examples of plasticizers comprise low molecular weight poly(alkylene oxides), such as poly(ethylene glycols), poly(propylene glycols), poly(ethylene/propylene glycols); organic plasticizers with a low molecular weight such as glycerol, pentaerythritol, glycerol monoacetate, diacetate or triacetate, propylene glycol, sodium diethyl sulfosuccinate and similar compounds added in concentrations of from 0.5 to 15, preferably from 0.5 to 5, % of the total weight of the drug form.

Different coloring of the various phases allows the forms to be made attractive with high recognizability. Examples of dyes are known azo dyes, organic and inorganic pigments, or coloring agents of natural origin. Inorganic pigments are preferred, in concentrations of from 0.001 to 10, preferably from 0.5 to 3, % of the total weight of the drug form.

Flavorings and aromas such as vanillin are preferably present in the carrier matrix.

It is also possible furthermore to add other additives which improve the flow properties of the mixture or act as mold release agents, eg. animal or vegetable fats, preferably in their hydrogenated form, especially those which are solid at room temperature. These fats preferably have a melting point of 50° C. or above. Triglycerides of $C_{12}$, $C_{14}$, $C_{16}$ and $C_{18}$ fatty acids are preferred. The same function can also be carried out by waxes such as carnauba wax. These additives can be added alone without addition of bulking agents or plasticizers. These fats and waxes can advantageously be admixed alone or together with mono- and/or diglycerides or phosphatides, especially lecithin. The mono- and diglycerides are preferably derived from the fat types described above, ie. $C_{12}$, $C_{14}$, $C_{16}$ and $C_{18}$ fatty acids. The total amount of fats, waxes, mono- and diglycerides and/or lecithins is 0.1–30, preferably 0.1–5, % of the total weight of the drug form.

Examples of flow regulators which can be used are aerosils or talc.

It is also possible furthermore to add stabilizers such as antioxidants, light stabilizers, hydroperoxide destroyers, radical scavengers and stabilizers against microbial attack.

Ancillary substances for the purpose of the invention also mean substances for producing a solid solution with the pharmaceutical active ingredient. Examples of these ancillary substances are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61, 69–88 (1986).

Bases or acids added to control the solubility of an active ingredient are also regarded as pharmaceutical ancillary substances (see, for example, K. Thoma et al., Pharm. Ind. 51, 98–101 (1989)).

Suitable active ingredients for the purpose of this invention are in principle all active ingredients which do not decompose under the processing conditions.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, w cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrin, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxypregesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, n-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin g, penicillin v, phenobarbital, pentoxifylline, phenoxymethylpenicillin, phenylephrine, phenylpropanolamine, phenytoin, piroxicam, polymyxin b, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin e, folinic acid, zidovudine, zotepine.

Active ingredients for the purpose of the invention are also vitamins and minerals, and crop treatment agents and insecticides. The vitamins include vitamins of A group, of the B group, by which are meant, besides $B_1$, $B_2$, $B_6$ and $B_{12}$ and nicotinic acid and nicotinamide, also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides.

In a few cases there may be formation of solid solutions. The term "solid solution" is familiar to the skilled worker, for example from Chiou and Riegelman, J. Pharm. Sci. 60, 1281–1302 (1971). In solid solutions, the active ingredient is in the form of a molecular dispersion in the matrix.

The active ingredient content per dose unit and the concentration may be varied within wide limits depending on the activity and release rate. The only condition is that they are sufficient to achieve the required effect. Thus, the active ingredient concentration can be in the range form 0.1 to 90, preferably from 0.5 to 60, .% by weight. These data likewise apply to the food supplement sector, such as vitamin products.

The formulations according to the invention can be produced as described below:

Firstly, the matrix components are converted into a plastic state. This may entail either a premix of all the components being plasticized, or first the polymeric binder being softened and then the other components, ie. active ingredients and/or other ancillary substances, being added thereto. The plasticization is effected by input of energy. Depending on the composition of the matrix, the components soften in the range from 40 to 190° C., preferably 50 to 150° C. The suitable temperature range in each case depends on the glass transition temperature of the polymeric binders, the properties of the active ingredients which are added where appropriate, and any plasticizers which are added. This is preferably done in the absence of solvents such as water or organic solvents. However, it may also be advisable to add small amounts of water as plasticizer. The optimal temperature range can be established by a few simple tests. The mixture of matrix components should soften so that the corresponding plastic material has a specific viscosity of from 0.0007 to 10,000 Pa.s, preferably 0.001 to 3000 Pa.s (at 150° C.).

The softening process can take place in an extruder, a kneader or a mixing reactor, with the plastic material being homogenized by longitudinal and transverse mixing.

The plasticization preferably takes place in an extruder having one or more screws which may rotate in the same direction or opposite directions, especially in a twin screw extruder. The latter can be operated with or without kneading elements, but use of kneading elements is preferred because mixing is better.

The particulate phase is added during the plasticization process. On use of an extruder, this can take place in the hot zone (hot feed) or in the cold zone. The particles are preferably fed in continuously via weigh feeders.

The temperature at which addition of the particulate phase takes place depends on the nature of the active ingredients and the type of release profiles required. If, for example, pellets are added, it may be desirable for these to melt on the surface because this leads to an increase in the surface area, which facilitates onset of the diffusion process after administration. On the other hand, however, the temperature should be low enough for separate phases to be maintained. The required temperature can be established by a few simple tests.

After incorporation of the particulate phase into the matrix phase, the still plastic material is shaped to the required dosage forms.

If, for example, it is wished to incorporate the particulate phase into a crystalline sugar matrix, it is advisable for the plastic material to be cooled, before the shaping, with stirring to such an extent that it can still be shaped but extrusion does not result in a quenched, amorphous, glassy melt.

The still plastic material can be extruded through a die or breaker plate and then shaped in a conventional way to tablets, chewable tablets, pastilles, buccal tablets, sublingual tablets, chewing compositions such as chewing gum or suppositories, or be packed in capsules. Shaping preferably takes place by calendering or by injection molding. Multilayer tablets can also be produced by the conventional coextrusion process. It is also possible to produce multilayer tablets by injection molding.

It is possible with the aid of the process according to the invention to produce in a simple manner dosage forms with very different release profiles.

The compositions have at least two phases, but may also contain several phases if different particulate phases are used.

It is thus possible, for example, to incorporate mutually incompatible active ingredients each as separate particulate phases. In this case, the surrounding matrix performs the function of an envelope and may be free of active ingredient.

In the case of active ingredients with very different physical properties, optimal particulate formulations of each can likewise be incorporated into one dosage form in a simple manner.

It is possible and particularly advantageous to produce dosage forms with stepped release profiles. Thus, for example, slow-release granules or pellets of an active ingredient can be incorporated into an instant release matrix, particularly beneficially into a solid solution, which likewise contains this active ingredient. It is possible in this way to achieve a rapid rise in level and a prolonged plateau-like release profile with one dosage form. Any desired sequence profiles can be adjusted by using granules of one and the same active ingredient but with different dissolving characteristics. It is also possible to adjust profiles with a delayed onset of release of active ingredient and repeat profiles.

Compared with conventional forms obtained by compression, the forms obtained from plasticized materials display better and, on production of solid forms, lower porosity and better mechanical stability.

EXAMPLES

General Method

The formulations according to the invention were produced in a twin screw extender (Werner & Pfleiderer ZSK-40, Stuttgart). The extruder consisted of a total of five separate temperature-controllable sections. The last section immediately before the die was provided with a feed port which was open at the top and through which the material was added to the plasticized melt. The melt was then extruded in the form of a ribbon through a 14 cm-wide slit die and passed immediately between two counter-rotating calender molding rolls. These molding rolls has on their surfaces depressions in the shape of half tablets, so that the ribbon of melt was shaped to a ribbon of tablets. The output of the extruder b was 20 kg/h. The screws rotated at from 80 to 130 revolutions per minute.

EXAMPLE 1

A mixture of 69% by weight of polyvinylpyrrolidone with a K value of 30, 30% by weight of ibuprofen and 1% by weight of highly disperse silica (Aerosil®200) was plasticized in the extruder at from 60 to 80° C. 6 kg/h of pure crystalline paracetamol were metered in through the feed port shortly before the die. The melt was transparent without added paracetamol, but became cloudy on addition of crystalline paracetamol, which did not dissolve therein. The melt was then shaped to oblong tablets with an average weight of 600 mg in the molding roll calender.

EXAMPLE 2

Oblong tablets were produced as in Example 1, but replacing pure crystalline paracetamol by crystalline paracetamol which had been film-coated with an isopropanolic solution of ethylcellulose.

EXAMPLE 3

A mixture of 25% by weight of ascorbic acid, 8% by weight of tocopherol acetate (TPSD 50 from BASF, 50% by weight formulation with a lactose/caseinate matrix), 30% by weight of hydroxypropylcellulose with an mw of 80,000 dalton (Klucel®EF from Aqualon), 14,4% by weight of isomalt F (from Palatinit, Mannheim), 1% by weight of lecithin, 1% by weight of orange flavor and 0.6% by weight of aspartame was extruded at 100–120° C. 4 kg/h of beta-carotene pellets with particle sizes in the range from 100 to 900$\mu$ (Betavit® from BASF, starch-dusted, 10% by weight beta-carotene formulation with a gelatin/lactose matrix) were metered in through the feed port before the die. The extruded melt was shaped to-oblong tablets with an average weight of 1000 mg in the molding roll calender. The red beta-carotene pellets were visible as separate particles in the tablet.

What is claimed is:

1. A solid or pharmaceutical composition comprising at least two phases, wherein one phase forms a matrix which consists essentially of one or more components selected from the group consisting of homo- or copolymer of N-vinylpyrrolidone, cellulose ether, hydroxyalkylcellulose, celluloseester and an acrylate- or methacrylate containing polymer and which contains at least one pharmaceutically active ingredient in the form of a solid solution and at least one other phase containing at least one active ingredient is homogeneously incorporated in the form of particles into the matrix phase.

2. The composition as claimed in claim 1, wherein said particles are in the form of crystals, pellets, microtablets or granules.

3. The composition as claimed in claim 1, wherein a flavoring is present in the matrix phase.

4. The composition as claimed in claim 1, which is obtained by incorporating the particles of said other phase into the matrix phase during or after plasticization and shaping the material while still plastic.

* * * * *